March 7, 1939. W. I. JOHNSTON Plant Pat. 317
ROSE
Filed Aug. 16, 1938
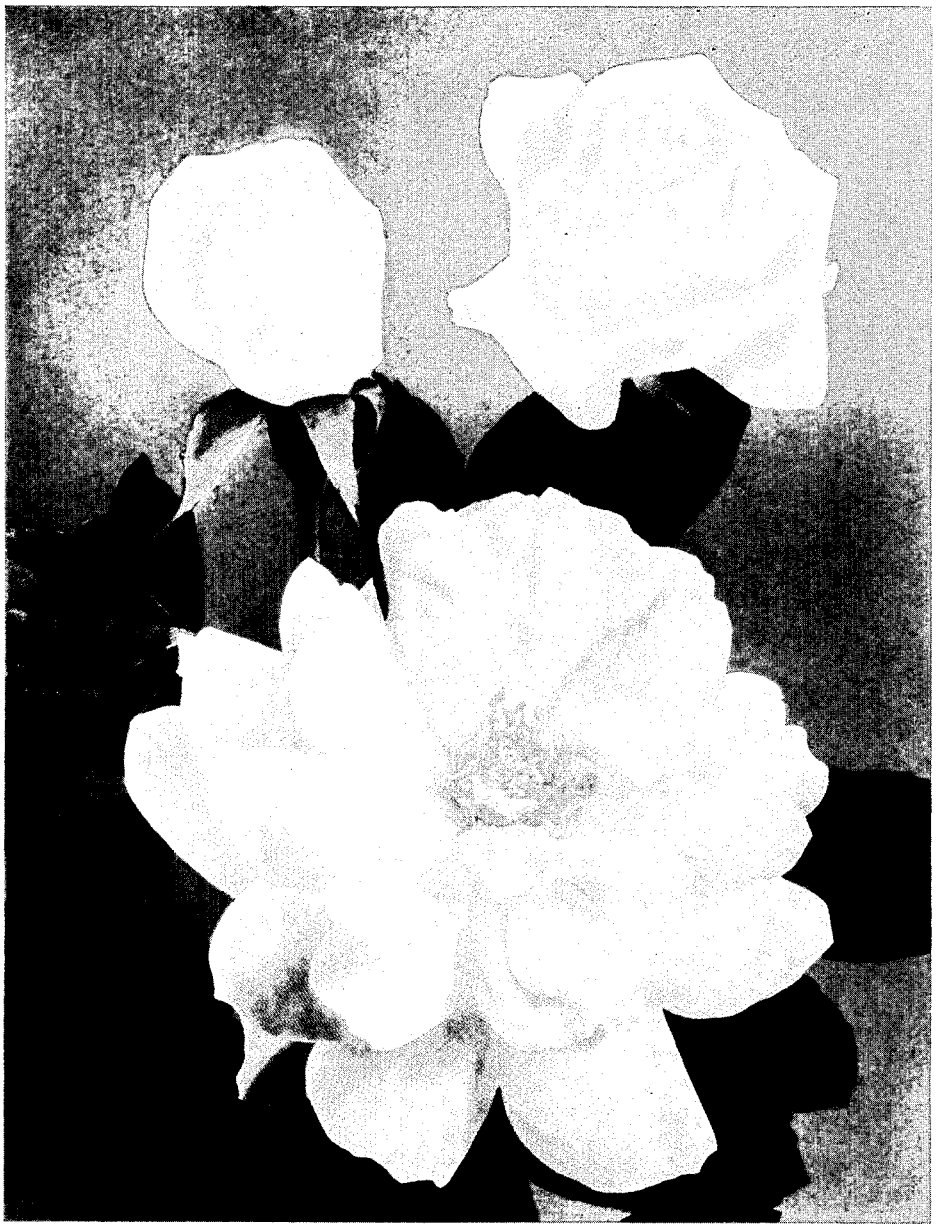
Inventor
W. I. Johnston
By Robb & Robb
Attorneys Patented Mar. 7, 1939

UNITED STATES PATENT OFFICE

317

ROSE

Walter Irwin Johnston, Portadown, Ireland, assignor to Jackson & Perkins Company, Newark, N. Y.

Application August 16, 1938, Serial No. 225,241

1 Claim. (Cl. 47—61)

The present invention relates to a new and distinct variety of hybrid tea rose originating from the crossing of two unnamed seedlings developed by the late Samuel McGredy and carried through extensive hybridizing by three generations of McGredys.

The McGredy's strain is noted for the great complexity of its ancestry due to the injection of new, strong blood, species, Hybrid Perpetuals, etc., and is the result of years of research and experimentation.

In the present instance, I have crossed two such developments primarily with the objective in view of obtaining an ideal growth for garden roses, characterized by uniform, beautifully formed flowers with new and different tones of coloring.

I have found this new variety to be the answer sought for in that it has, among its other attributes, the high coloring, glossy foliage and hardiness of the Pernetiana strain. The general mass effect produced by it is a bed of yellow-orange bloom, very distinctive and quite different from anything now known of comparable characteristics.

The new variety produces a healthy vigorous bush of medium height with medium size, well balanced foliage, is easy to grow and superior to many other roses due to its fine plant and plant habits.

It will be noted from the accompanying illustration that the color of the flower is unique, and it has the added value of retaining its intensity even in the hottest and driest weather.

Another important feature of my new variety is the elimination of susceptibility to "black spot" and other diseases.

This new variety has been asexually reproduced and its characteristics hereinafter described have been found to be fixed.

The following is a detail description of the new variety, all references to color being in accord with Ridgway's Color Standard:—

Parentage:

*Seed parent and pollen parent.*—Unnamed seedlings of the McGredy Strain.

Classification:

*Botanic and commercial.*—Hybrid Tea.

*Flower*

(Observations made in fields and gardens of Jackson & Perkins Company, Newark, New York.)

Blooming habit:

Recurrent—intermittent.

Bud:

*Size.*—Medium.

*Form.*—Ovoid; is not affected by wet or hot weather.

*Color.*—When sepals first divide—Mikado Orange (Plate III); when petals begin to unfurl—Capucine Orange (Plate III); when half blown: inside of petals—Cadmium Yellow (Plate III); reverse of petals—Capucine Orange (Plate III).

*Sepals.*—Smooth edge; curl back when bud starts to open.

*Calyx.*—Shape — apple; size — long, small; aspect—smooth.

*Peduncle.*—Length—medium; aspect—smooth; color—Light Cress Green (Plate XXXI); strength—erect.

*Opening.*—Bud opens well; is not affected by adverse conditions.

Bloom:

*Size.*—Medium.

*Average size when fully expanded.*—Four to five inches.

*Borne.*—Singly and several together.

*Stems.*—Medium length, strong.

*Form.*—When first open—cupped; permanence—flattens.

*Petalage.*—Double (full but open center). Number of petals under normal conditions—25 to 35.

*Color.*—Center of flower—Lemon Chrome (Plate IV) to Deep Chrome (Plote III); outer petals—Light Orange Yellow (Plate III) to Orange (Plate III); base of petals (aiglet)—Lemon Yellow (Plate IV); inside of petals—Cadmium Yellow (Plate III); reverse of petals—Deep Chrome (Plate III); general tonality from a distance—Cadmium Yellow (Plate III).

*Variegations.*—None.

*Discoloration.*—General tonality at end of first day—Light Cadmium (Plate IV); second day—Lemon Chrome (Plate IV); third day—Empire Yellow (Plate IV).

Petals:

*Texture.*—Thick; is not affected by wet or hot weather.

*Appearance.*—Inside—shiny; outside—shiny.

*Form.*—Oval.

*Arrangement.*—Informal (with "rags" in center); petaloids in center—few, small.

*Persistence.*—Drop off cleanly.

*Fragrance.*—Moderate; nature—fruity (Russet apple).

*Lasting Quality.*—On the plant and as cut flower, long.

Genital organs:

*Stamens, anthers.*—Large, many; color—Cadmium Yellow (Plate III); arrangement—regular around styles.

*Stamens, filaments (threads).*—Long; color—Lemon Yellow (Plate III).

*Pollen.*—Cadmium Yellow (Plate III).

*Styles.*—Bunched, medium length, thin.

*Stigmas.*—Light Orange Yellow (Plate III).

*Ovaries.*—All enclosed in calyx.

Fruit:

Variety is fertile with its own pollen.

*Form.*—Ovid.

*Aspect.*—Smooth.

*Color at maturity.*—Deep Chrome (Plate III).

*Sepals.*—Caducous (soon falling), recurved.

*Plant*

Form:

Bush.

Growth:

Vigorous, branching.

Foliage:

5 to 7 leaflets.

*Size.*—Medium.

*Quantity.*—Normal.

*Color.*—New foliage: upper side—Dark Cress Green (Plate XXXI); under side—Cress Green (Plate XXXI). Old foliage: upper side—Chromium Green (Plate XXXII); under side—Rainette Green (Plate XXXI).

*Shape.*—Oval.

*Texture.*—Upper side—glossy; under side—smooth. Ribs and veins—ordinary.

*Edge.*—Serrated (saw toothed).

*Serration.*—Single, small, sharp.

*Rachis.*—Color—Garnet Brown (Plate I) over Cress Green (Plate XXXI); under side—prickles.

*Stipules.*—Medium, bearded.

*Disease Resistance.*—Resistant.

Wood:

*New Wood.*—Color—Cress Green (Plate XXXI); bark—smooth.

*Old Wood.*—Color—Spinach Green (Plate V); bark—smooth.

Thorns (divided into thorns, prickles, and short needles):

*Thorns.*—Quantity: on main stalks from base—few; on laterals from stalk—few. Form—broad base, medium length, hooked downward. Color when young—Cress Green (Plate XXXI). Position—irregular.

*Prickles.*—Quantity: on main stalks—few; on laterals—few. Color—Cress Green (Plate XXXI).

*Short Needles.*—Quantity: on main stalks and laterals—few.

I claim:

A new distinct variety of hybrid tea rose, characterized by vigor of growth, its healthy foliage, its upright growth, all adapting it for bedding and massing, the freedom and persistency in its blooming, and its striking orange-yellow color, substantially as shown and described.

WALTER IRWIN JOHNSTON.